United States Patent [19]

Shimoni et al.

[11] Patent Number: 5,125,015

[45] Date of Patent: Jun. 23, 1992

[54] METHOD AND SYSTEM FOR DETERMINING A LOWER-BOUND DENSITY OF A BODY

[75] Inventors: Yair Shimoni, Yahud; David Vartsky, Rehovot; Yair Shamai, Rehovot; Acher Sayah, Rehovot, all of Israel

[73] Assignee: The State of Israel Atomic Energy Commission, Soreq Nuclear Research Center, Yavne, Israel

[21] Appl. No.: 645,982

[22] Filed: Jan. 23, 1991

[30] Foreign Application Priority Data

Jan. 26, 1990 [IL] Israel ..................................... 93188

[51] Int. Cl.$^5$ ............................................ G01N 23/06
[52] U.S. Cl. ......................................... 378/51; 378/53; 378/57; 378/56; 378/54
[58] Field of Search ..................... 378/51, 53, 54, 55, 378/57, 31, 99

[56] References Cited

U.S. PATENT DOCUMENTS 4,941,162 7/1990 Vartsky et al. ..................... 378/3
5,022,062 6/1991 Annis ................................. 378/86

*Primary Examiner*—Janice A. Howell
*Assistant Examiner*—Kim-Kwok Chu
*Attorney, Agent, or Firm*—Helfgott & Karas

[57] ABSTRACT

A method for determining a lower-bound quantity per unit volume of a physical property associated with a body, the property being susceptible to measurement in a plurality of directions. In general, the method comprises the steps of scanning a volume of interest in a predetermined number of directions so as to derive for each direction an area having a plurality of projections thereon each representing a cumulative value of said property within the volume of interest along a respective one of the directions, and determining an estimated volume of the body as the intersection of all volume elements bounded by the derived areas. For each area the sum of all the projections are compared and correction is applied as required so as to remove any disparity between the sums so as to produce a uniform sum in each of the directions. The lower-bound quantity per unit volume of the property of the body is then calculated as the quotient of the uniform sum divided by the estimated volume. A system is also described for determining the lower-bound density of nitrogen using the method according to the invention.

30 Claims, 9 Drawing Sheets

METHOD AND SYSTEM FOR DETERMINING A LOWER-BOUND DENSITY OF A BODY

FIELD OF THE INVENTION

This invention relates to a method and system for determining a lower-bound quantity per unit volume of a physical property associated with a body. In particular, it relates to a method for determining the lower-bound density of a substance within a volume of interest.

BACKGROUND OF THE INVENTION

There exists a need to determine the lower-bound density of a substance within a volume of interest from a number of different projections of a body containing the substance. In this context, a "projection" is obtained by scanning the volume of interest with penetrating radiation across several predetermined areas so that each scan permits the mass of the substance encountered by the scanning medium to be determined. In this case, each projection gives the total mass of the substance encountered along the respective line of sight of the projection.

Examples where such techniques may be employed include medicine where, for example, tumours may have a different density from that of the surrounding healthy tissue. Thus, it is possible to discriminate between the tumour and the healthy tissue by determining the lower-bound density of all tissue within a volume containing the suspected tumour. The terms "mass" and "density" are used here as an example of any property of the volume of interest which is measured by the scanning medium. Thus, explosives containing high proportions of particular elements or molecules may be discriminated from other materials by determining the lower-bound density of the particular elements or molecules of all objects within a suspected volume.

Prior art systems for discriminating between different bodies within a given volume are typically based on a tomographic analysis of images derived from a series of many projections or views. Such an approach requires the use of complex algorithms which is time-consuming and the further need to view the volume of interest from many different angles adds significantly to the cost, the duration of the test and the radiation dosages required.

In U.S. Pat. No. 4,941,162 (Vartsky et al.) there is described a method and system for the detection of a nitrogenous explosive material in an object. The method described by Vartsky et al. involves scanning the object with a $\gamma$-ray beam derived from a suitable source of radiation disposed on one side of the object, and detecting resonant attenuations of the incident photon flux produced by that beam on an array of detectors having a nitrogen rich detecting medium. In such a method, an explosive material containing a large volume of nitrogenous material produces a high reading on the detector, whilst non-nitrogenous materials produce a low reading or no reading at all. As is well known, for penetrating electromagnetic radiation such as $\gamma$-rays, $$\ln\left(\frac{I_o}{I_d}\right) = A \int_o^D K \cdot \rho_a \, dx = A \cdot K \cdot m_a$$

where:
D = distance of detector from source
x = line of sight
$I_o$ = incident flux
$I_d$ = detected flux
A = constant of proportionality
K = absorption constant
$\rho_a$ = density of absorbing atom
$m_a$ = cumulative mass along line of sight of absorbing atom.

For resonant attenuation, the density of all but the resonating atom may be neglected and the above logarithm is proportional to the integral along the line of sight of the resonating atom's density, i.e. its mass.

The present invention finds application, inter alia, in analysing the image data produced by such a method in order to discriminate between nitrogenous explosives and other material, based on the nitrogen density.

There exists a continuing need in airport security systems to provide fail-safe systems for identifying explosives within passengers' luggage. Such methods and systems are subject to two stringent requirements. On the one hand, they must be sufficiently sensitive that they successfully identify explosives which, if not otherwise located, would constitute a security risk. At the same time, they must not be so sensitive that they give false alarms since even a very small failure rate, giving rise to a false alarm, is unacceptable in airport security systems. This will be understood, more clearly, when it is considered that for each suitcase containing an explosive, there are some $100 \times 10^6$ which are perfectly safe. Thus, a failure rate of only one in a thousand will yield 100,000 false alarms to each true alarm, which is clearly quite unacceptable.

BRIEF SUMMARY OF THE INVENTION

It is an object of the invention to provide a method and system for determining a maximum lower-bound nitrogen density associated with a body so as to permit an alarm to be raised in the event that the calculated value is commensurate with the body being an explosive.

According to a broad aspect of the invention, there is provided a method for determining a lower-bound quantity per unit volume of a physical property associated with a body, said property being susceptible to measurement in a plurality of directions, the method comprising the steps of:

scanning a volume of interest in a predetermined number of directions so as to derive for each direction an area having a plurality of projections thereon each representing a cumulative value of said property within the volume of interest along a respective one of the directions, determining an estimated volume of the body as the intersection of all volume elements bounded by said areas, comparing for each area the sum of all the projections and applying correction as required so as to remove any disparity between said sums and produce a uniform sum in each one of said directions, and determining the lower-bound quantity per unit volume of said property of the body as the quotient of the uniform sum divided by the estimated volume.

Thus, if the method according to the invention is employed in an airport security system such as described in the above-mentioned U.S. Pat. No. 4,941,162 the maximum lower-bound nitrogen density of all objects within a suitcase may be determined and this may then be compared with a predetermined threshold corresponding to an unacceptably dangerous level of explosive material. If the measured lower-bound nitrogen density exceeds this threshold, and only under these circumstances, an alarm may be issued consequent to which a manual search of the suspect luggage will then be conducted or other security measures will be taken.

It will further be understood that by determining only the lower-bound density, all errors tend to minimize the measured density rather than to exaggerate it. This is highly important if false alarms are not to be generated on account of registering unrealistically high densities.

By considering only the maximal lower-bound density, the mathematical problem is greatly simplified requiring the volume of interest to be scanned in a relatively small number of directions as compared with conventional tomographic approaches. Consequently, the method according to the invention is faster, more reliable and cheaper than conventional tomography.

BRIEF DESCRIPTION OF THE DRAWINGS

The invention will now be described, by way of non-limiting example only, with regard to a method for determining the maximum lower-bound nitrogen density of a body contained within a suitcase having an assortment of objects therein and with reference to the accompanying drawings, in which.

DETAILED DESCRIPTION OF A PREFERRED EMBODIMENT

Figure 1:
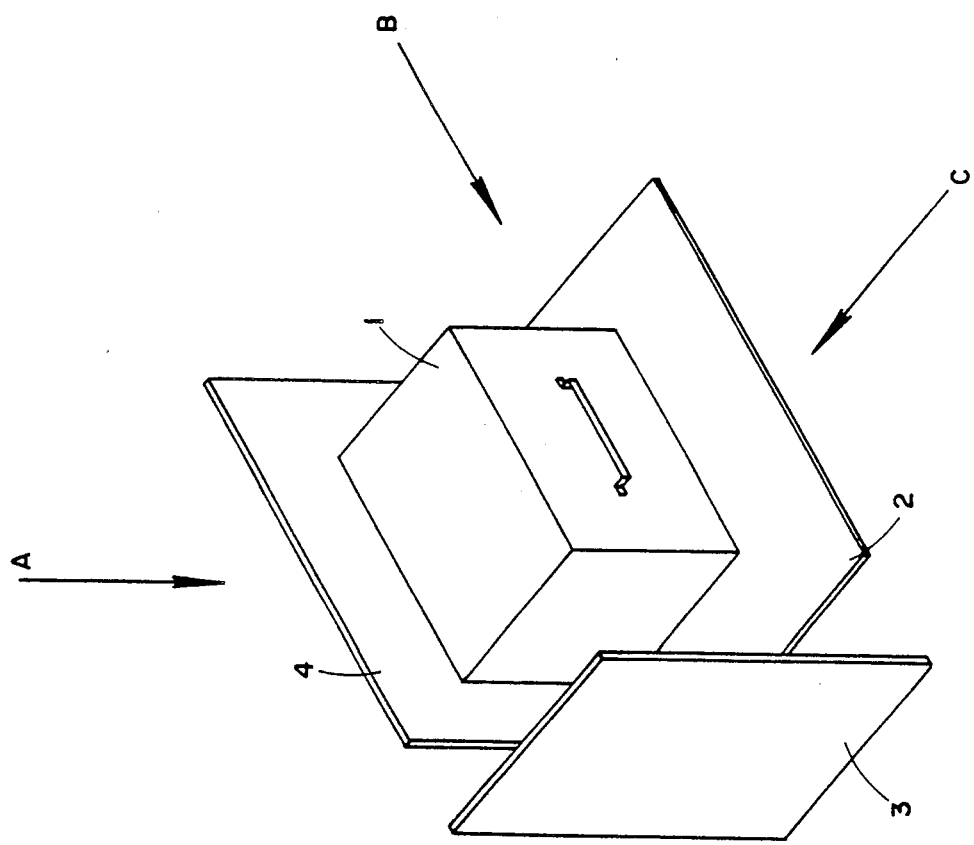
FIG. 1 shows schematically a perspective view of an arrangement for determining the lower-bound density of a body according to the invention.

Referring to FIG. 1, there is shown a suitcase 1 which is scanned by suitable sources (not shown) of electromagnetic penetrating radiation at the frequency of resonant absorption by nitrogen, in directions A, B and C so as to produce corresponding images on respective area-image sensors 2, 3 and 4, disposed normal to the directions A, B and C, respectively. Each of the area-image sensors 2, 3 and 4 comprises an array of pixels which are illuminated according to the mass of nitrogen encountered by the beams of electromagnetic radiation emanating from the respective sources as they pass through the suitcase 1. Thus, the total mass encountered in the direction A on the area-image sensor 2 represents the total mass of nitrogen within the suitcase 1. Ignoring any slight differences in the nature of the detectors and assuming that the magnification factors for all the detectors are identical, the total mass encountered in the direction A must clearly be equal to the mass encountered in the direction B as indicated on the area-image sensor 3 and, likewise, the mass encountered in the direction C on area-image sensor 4.

In practice, it may happen that the total mass quantities registered on each of the three area-image sensors 2, 3 and 4 are unequal owing to the effects of magnification, pixelization and background noise. Therefore the image data obtained from the three area-image sensors 2, 3 and 4 are first processed in order to equalize the cumulative mass recorded on each sensor. The manner in which the image data on the three area-image sensors 2, 3 and 4 are derived and pre-processed so as to remove the effects of noise and pixelization is not a feature of the present invention and so will not be described in greater detail.

Typically, the sources of radiation produce intersecting cones of radiation wherein it is known that there exists a body of unknown shape and density containing nitrogen. However, without further processing, it is not known whether the total mass of nitrogen is contained in one body or in several, whether there exists a cross-effect between more than one body in the path of one of the beams of radiation which gives rise to a cumulative mass in excess of the discrete masses associated with the bodies separately, or if the nitrogen density of the body indicates it is an explosive.

Figure 2:
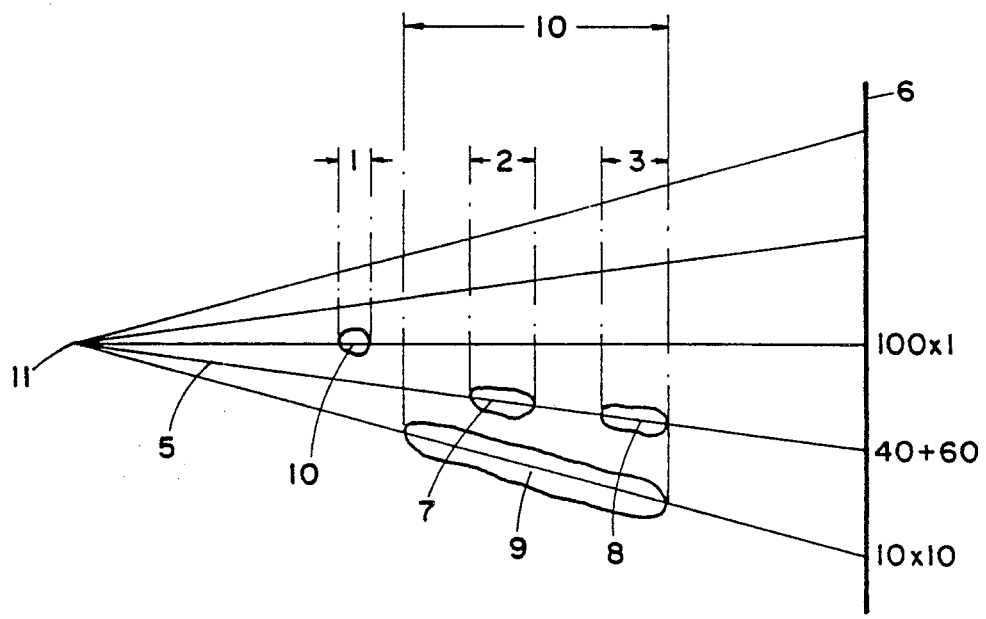
FIG. 2 shows schematically a cross-section of an area-image sensor having an image of multiple bodies thereon.

Referring now to FIG. 2, there is shown a cross-section through an area-image sensor 6 shown in FIG. 1, illustrating schematically the effect of passing a beam 5 through several bodies 7, 8, 9 and 10 containing nitrogen. The beam 5 is derived from a source 11 of $\gamma$ radiation at the resonant frequency of nitrogen and the intensity of each pixel on the area-image sensor 6 is given, after the necessary transformations, by $C(i,j)$ where:

$$C(i,j) = \int_0^L \rho(s)ds$$

where:

$\rho(s)$ is the nitrogen density encountered by the beam at a distance s from the source, and L is the distance from the source to the area-image sensor.

Thus, the greater the distance through each body traversed by the beam of radiation 5 en route from the source 11 to the area-image sensor 6, the greater will be the measured response of the corresponding pixel intersected by the corresponding ray within the radiation beam. Assuming that the densities of the bodies 7 and 8 are both equal to 20 and the length of the beam 5 passing through the bodies 7 and 8 is respectively equal to 2 and 3, then the cumulative mass registered on the area-image sensor 6 is given by:

$$C = 20 \times 2 + 20 \times 3 = 100$$

Likewise, if it be assumed that the density of the body 9 is equal to 10 and the length of the beam 5 passing therethrough equals 10, then the cumulative mass associated with the projection of the beam 5 is also equal to 100. Similarly, if the density of the body 10 is equal to 100 and the length of the projection of the beam 5 passing therethrough is equal to 1, then the cumulative mass corresponding to the beam 5 passing through the body 10 is also equal to 100.

Consequently, on the area-image sensor 6 there are three pixels representative of a cumulative mass equal to 100. Clearly, only the body 10 having a nitrogen density of 100 is of interest, since if its density exceeds the threshold density, it is not necessary to relate to any of the other bodies having a lower density and if its density is less than the threshold density, then clearly so, too, will the densities of the other bodies 7, 8 and 9.

Figure 3:
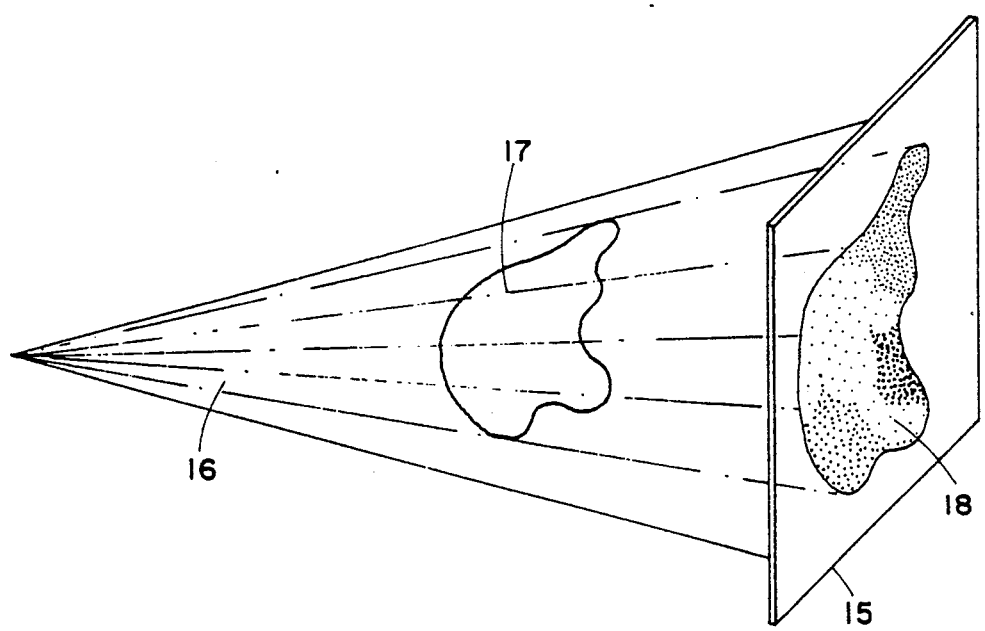
FIG. 3 is a pictorial representation showing a first step in an algorithm according to the invention.

Referring to FIG. 3, there is shown pictorially an area-image sensor 15 showing two-dimensional image data derived from passing a beam of radiation 16 through the suitcase 1 in one direction. The shading shown in FIG. 3 corresponds to the cumulative mass encountered by each ray emanating from the source of radiation and passing through a body 17 so as to form an image 18 on the area-image sensor 15. Thus, associated with each area of shading on the area-image sensor 15 are pixels having different intensities corresponding to the cumulative mass encountered by the respective rays striking the pixels.

Figure 4:
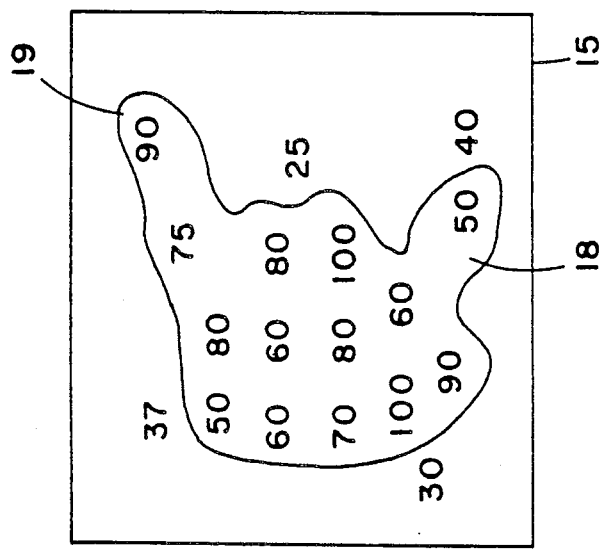
FIG. 4 relates to FIG. 3 and shows schematically a process for identifying significant bodies within a test volume.

FIG. 4 relates to FIG. 3, and shows schematically the image 18 on the area-image sensor 15. The numbers depicted on the area-image sensor 15 correspond to the cumulative masses associated with corresponding pixels and, clearly, the drawing is shown at a highly exaggerated scale. In a preliminary step of the algorithm, only pixels corresponding to a cumulative mass greater than a predetermined threshold $T_1$ are considered and in FIG. 4 it is assumed that only cumulative masses greater than 50 are of interest. There thus exists a boundary 19 separating all pixels for which the cumulative mass exceeds the threshold 50 from those whose mass is less than this threshold. Any image data outside of the boundary 19 is no longer of interest and thus in subsequent steps of the algorithm, attention is paid only to the image data within the boundary 19.

Although in FIGS. 3 and 4 only one body 17 is shown corresponding to the boundary 19, it should be understood that in reality there may exist several discrete boundaries on the area-image sensor 15 corresponding to respective bodies within the test volume, for which the cumulative mass as measured on the area-image sensor 15 exceeds the threshold. In this more general case, it is necessary to determine the lower-bound density of each discrete body so as to identify the body having the maximum lower-bound density, and then to determine whether this maximum lower-bound density exceeds the threshold density. One way in which this may be done will now be described.

Figure 5:
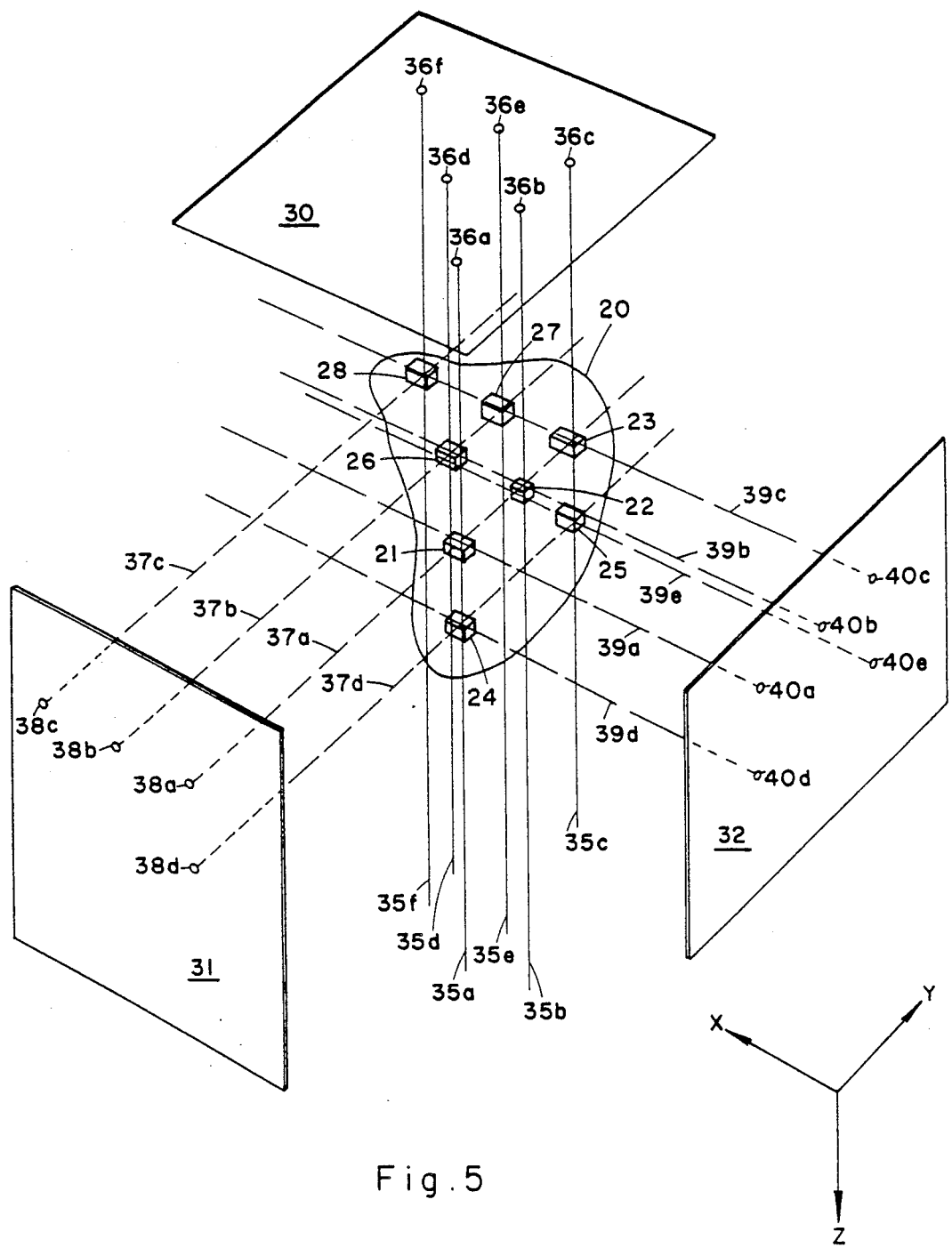
FIG. 5 shows pictorially a test volume for which the lower-bound density of its constituent bodies may be determined iteratively.

Referring to FIG. 5, there is shown schematically a body 20 containing eight volume elements, or "voxels", 21, 22, 23, 24, 25, 26, 27 and 28. Also shown are three area-image sensors 30, 31 and 32 which are disposed in mutually orthogonal planes. It should be understood, however, that orthogonality is not a requirement and nor do the three area-image sensors have to be planar. Associated with each of the three area-image sensors 30, 31 and 32 are rays of electromagnetic radiation emanating from corresponding sources (not shown) which pass through the voxels 21 to 28 so as to strike corresponding pixels on the area-image sensors. In the example all the rays are shown as being parallel although this is not a requirement in practice.

A Cartesian co-ordinate frame (x,y,z) is shown such that the area-image sensor 30 is in the x-y plane, the image-sensor 31 is in the x-z plane and the image-sensor 32 is in the y-z plane. In the following description it will be assumed that the (x,y,z) co-ordinates of the voxels 21 to 28 are as follows:

21: (1,1,1)
22: (1,2,1)
23: (1,3,1)
24: (1,1,2)
25: (1,3,2)
26: (2,2,1)
27: (2,3,1) and
28: (3,3,1).

Thus, the ray 35a passes through the voxels 21 and 24 so as to strike a pixel 36a on the area-image sensor 30. Likewise, a ray 35b passes through the single voxel 22 so as to strike a pixel 36b on the area-image sensor 30. In a similar manner, it can be shown that rays 35c, 35d, 35e, and 35f pass respectively through voxels (23, 25), 26, 27 and 28 so as to strike corresponding pixels 36c, 36d, 36e and 36f on the area-image sensor 30.

Similarly, it can be shown that rays 37a, 37b, 37c and 37d pass respectively through the voxels (21, 22 and 23), (26 and 27), 28 and (24 and 25) so as to strike corresponding pixels 38a, 38b, 38c and 38d on the area-image sensor 31 whilst rays 39a, 39b, 39c, 39d and 39e pass respectively through voxels 21, (22 and 26), (23, 27 and 28), 24 and 25 to strike corresponding pixels 40a, 40b, 40c, 40d and 40e on the area-image sensor 32.

Thus, the number of voxels intersected by each of the rays onto the three area-image sensors 30, 31 and 32 are as follows:

| Image plane | Co-ordinates | Number of Voxels |
|---|---|---|
| x(y,z) | (1,1) | 1 |
|  | (2,1) | 2 |
|  | (3,1) | 3 |
|  | (1,2) | 1 |
|  | (3,2) | 1 |
|  |  | 8 |
| y(x,z) | (1,1) | 3 |
|  | (2,1) | 2 |
|  | (3,1) | 1 |
|  | (1,2) | 2 |
|  |  | 8 |
| z(x,y) | (1,1) | 2 |
|  | (1,2) | 1 |
|  | (1,3) | 2 |
|  | (2,2) | 1 |
|  | (2,3) | 1 |
|  | (3,3) | 1 |
|  |  | 8 |

For the sake of clarity and explanation, the rays 35a, 35b and 35c, etc., are shown as being parallel as if derived from a collimated beam of radiation or from a very distant source. However, the actual geometry of the beam of radiation is not important so long as it is known and determined, thereby permitting determination of each voxel within the volume of interest associated with each ray. Thus, if the position of the source of radiation is known with respect to the volume of interest, and if the geometry of the beam is known, it is a simple geometric exercise to determine, for each ray emanating from the source, through which voxels the ray will pass.

The "traverse" of each ray is equal to the number of voxels contained within the volume of interest 20 through which the ray passes. Thus, the traverse of the ray 35f is equal to one since it passes through only one voxel 28, whilst the traverse of the ray 39c is equal to 3 since it passes through three voxels 23, 27 and 28.

Thus, having determined that the traverse of ray 35f is equal to one, the cumulative mass corresponding to the one pixel 36f may be completely associated with the voxel 28. Consequently, the lower-bound density of the elemental body corresponding to the voxel 28 is equal to the mass associated with the pixel 36f divided by the volume of the voxel 28. If this lower-bound density exceeds the threshold, no further processing is required since it is then clear that the suitcase contains an explosive.

However, if the calculated density is less than the threshold density, further processing is required, as follows. The voxel 28 is eliminated from the test volume corresponding to the body 20, the mass associated with the pixel 28a being subtracted from each of the projections corresponding to the rays (37c and 39c) so as to correct the respective cumulative masses associated with the pixels 38c and 40c. After this subtraction, each of the projections thus modified is checked. If the new mass is zero, or under the threshold $T_1$, then any voxel along the corresponding ray is eliminated. An exactly similar procedure may be effected for the voxel 21, since the ray 39a passing through this voxel and striking the pixel 40a also has a traverse exactly equal to one. Therefore, the voxel 21 may be eliminated from the volume of interest and the mass associated with the pixel 40a may be subtracted from the masses associated with the pixels 36a and 38a.

Having done this, the ray 35a passes through only one voxel 24 so that it also now has a traverse equal to one. Thus, the corrected mass on the area-image sensor 30 corresponding to the pixel 36a, now corresponds to the mass associated with the voxel 24. Its density may now be calculated and, if less than the threshold density, the voxel 24 may be eliminated from the volume of interest, leaving a single voxel 25 along the ray 37d. Therefore, the voxel 25 may also be determined and eliminated, leaving a single voxel 23 along the ray 35c.

In like manner, the densities of each of the voxels within the body 20 may be calculated and the voxels eliminated from the volume of interest if their densities do not exceed the threshold. In the above procedure, the order in which voxels are eliminated from the volume of interest is optional since this step in the algorithm is deterministic and not convergent.

At the end of the above process, only those rays remain which pass through more than one voxel and only those voxels remain that are not the only voxels through which a ray passes. If there are no such remaining rays and voxels, then the examination of the suitcase 1 (FIG. 1) is complete and a new suitcase may be scanned. If, however, there exists remaining, unelimi- nated rays and voxels, then the algorithm continues as follows.

For each ray in the volume of interest, the ratio is calculated between the cumulative mass in the pixel corresponding to the ray and the traverse length of that ray. That is, the cumulative mass is divided into the number of uneliminated voxels the ray has traversed. If the mass is in fact divided evenly along the ray in the uneliminated voxels, the above ratio equals the density (mass per voxel). Otherwise, somewhere along the ray, the density must be higher than the above ratio. The above ratio is therefore a lower-bound for the maximum density along the ray. The maximal ratio found for any pixel (i.e. in the ray) is therefore a lower-bound for the maximum density in the body. If this maximum ratio exceeds the threshold density, then somewhere inside the volume of interest there exists a region whose nitrogen density exceeds the threshold and an alert signal is generated. If the maximum ratio does not exceed the threshold density this indicates that an explosive has not yet been detected.

Figure 6A:
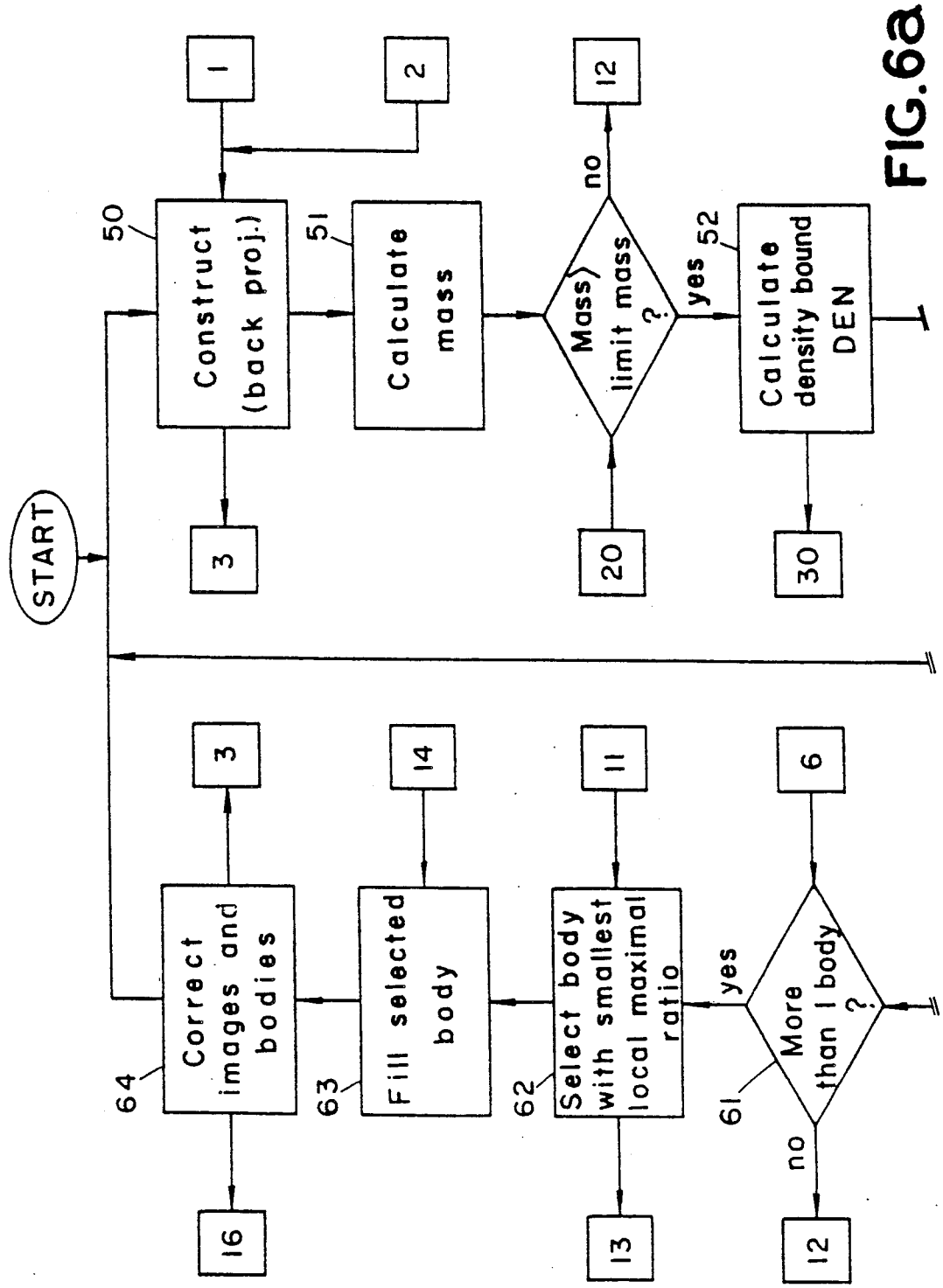
FIGS. 6a, 6b, 7 and 8 show a flow diagram of an algorithm for determining the maximum lower-bound density within a test volume according to the invention.
Figure 6B:
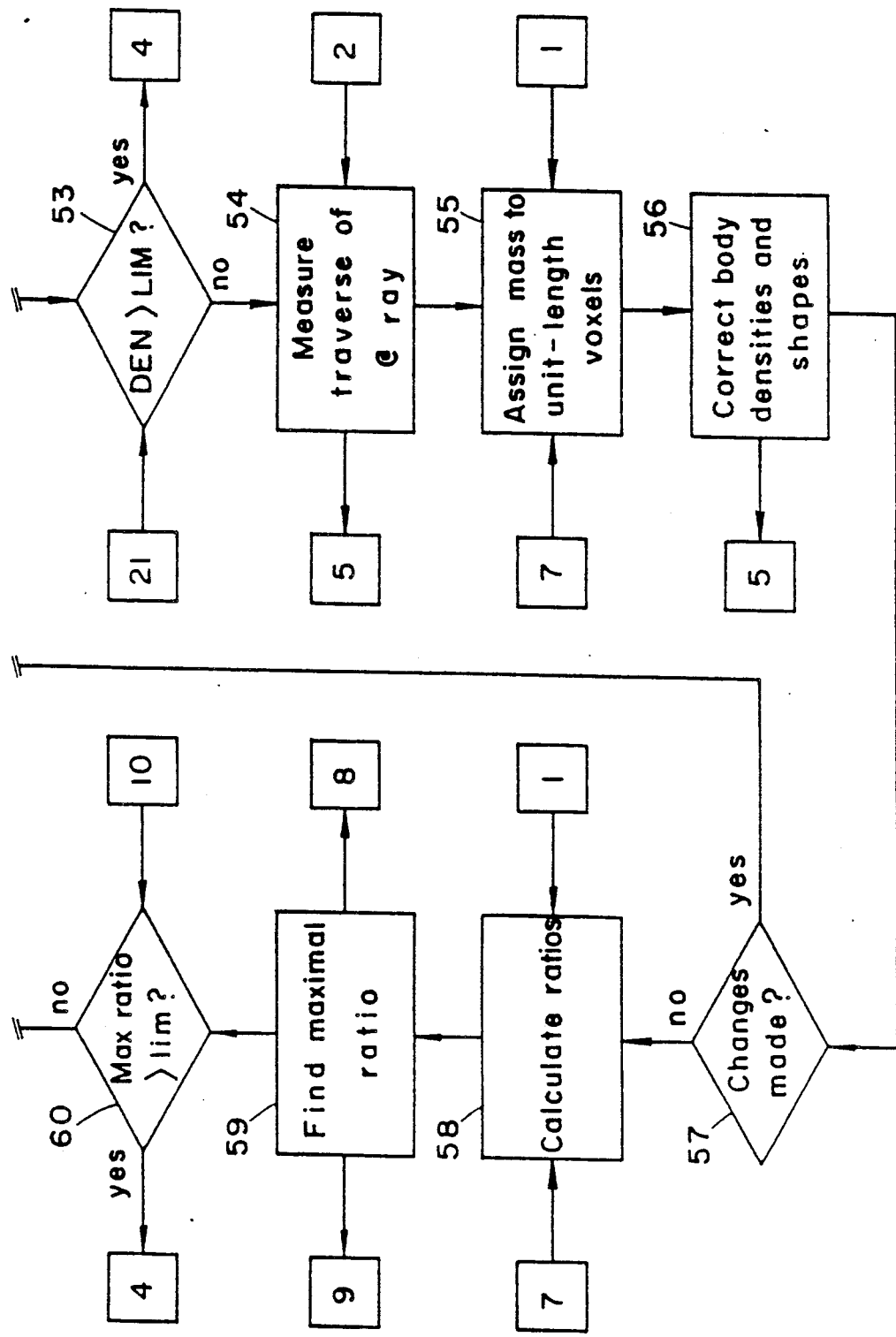
Figure 7:
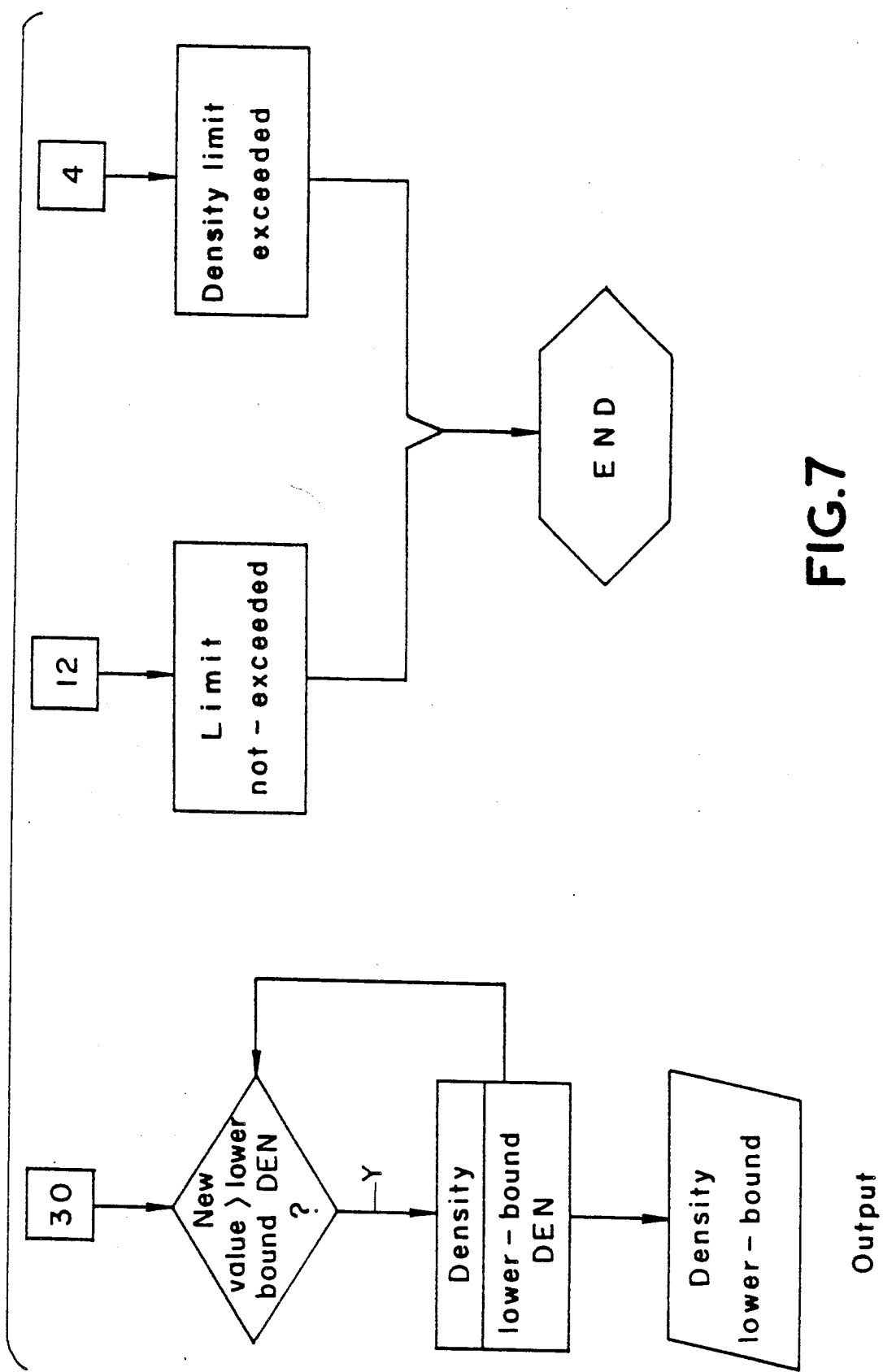
Figure 8:
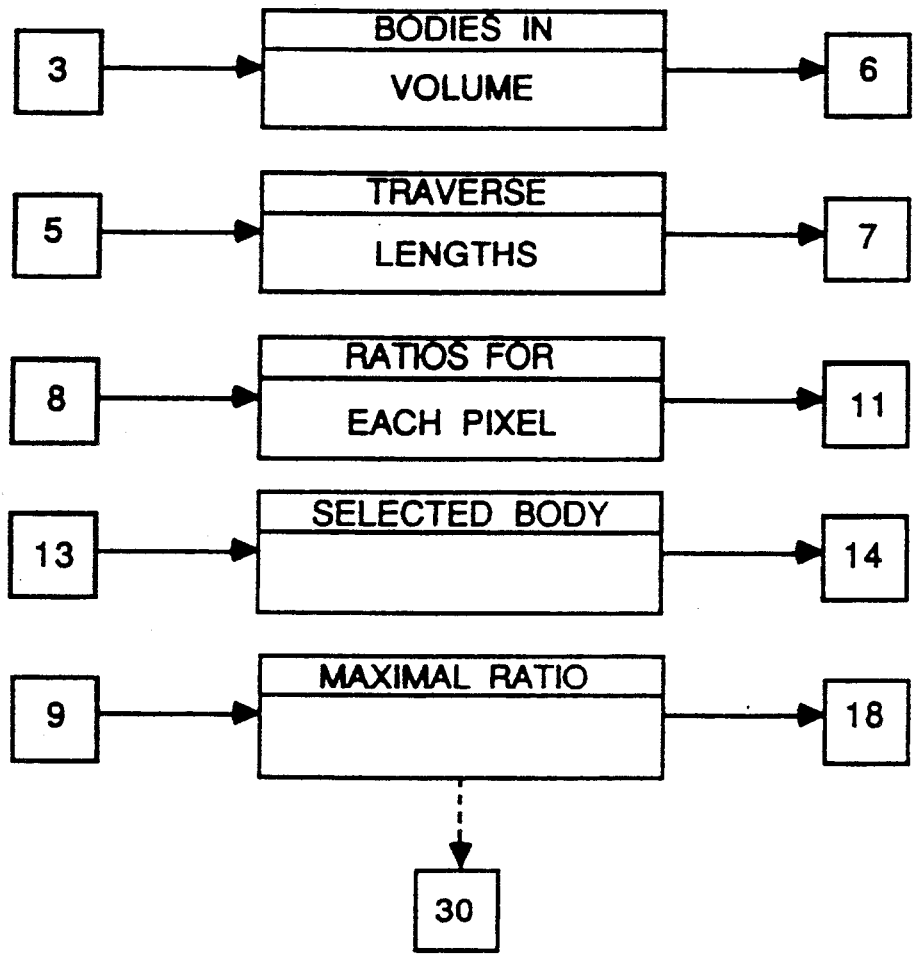

FIGS. 6a and 6b forming a complete single figure and FIGS. 7 and 8 show a flow chart of an algorithm for processing the image data shown, for example, in FIG. 5 so as to determine the maximum lower-bound density of all bodies contained within the test volume. In step 50, a test volume is constructed as the intersection of the three cones defined by the respective sources of radiation and the boundaries of the regions of interest on the area-image sensor, such as 19 in FIG. 4. Only information contained within this volume is of interest and is subsequently processed.

In step 51 the cumulative mass is derived for each area-image sensor by adding all the masses within the region of interest (depicted in FIG. 4 by the boundary 19), wherein the masses exceed the predetermined threshold. As explained above, the cumulative mass in each image must be identical and therefore the images are corrected so as to remove any disparities and are also normalized in order to correct for any errors caused by the beam geometry. Thus, a fan-shaped beam causes magnification on the area-image sensor on account of the fact that it spreads out and this must be corrected for before further processing is undertaken. The correction for the magnification depends on the distance between the volume of interest and the detector and is different for the different images. The use of a collimated source of radiation, resulting in a parallel beam, avoids this problem.

It should be noted that the mass calculated in step 51 will not generally be completely accurate on account of very small or rare masses (i.e. having low density) which are included in one view but not in any others. It is assumed that the effect of such small or rare masses is insignificant. If the cumulative mass in the volume of interest is less than a limit mass then, even if it contains explosive material, its quantity is insufficient to constitute a danger. In this case, the process is terminated at [12] without sounding an alarm.

The boundary 19 shown in FIG. 4 depicts an area within which the projected mass exceeds the predetermined threshold. Consequently, by considering the volume elements or "voxels" contained within a volume of intersection defined by the cone of light emanating from the respective radiation sources and each having a base defined by the corresponding boundary 19 on the respective area-image sensor, the maximum volume containing the body may be determined. The lower-bound density of this body is then determined as the quotient of the cumulative mass divided by the maximum volume. This corresponds to step 52.

In step 53, the lower-bound density calculated in step 52 is compared with a predetermined density threshold such that processing ceases in the event that the calculated density exceeds the density threshold. In this case, it is assumed that the body contains explosive material and a suitable alarm signal will be generated. If the calculated density does not exceed the density threshold, further processing is required since it is not yet known whether the "body" processed so far does, in reality, have a density lower than the density threshold. In the previous steps, 50 to 53, only global tests were used. Much more effective local tests are now performed.

Thus, in step 54 the traverse of each ray is determined, to be used in step 55 to force, as described in detail with reference to FIG. 5, all voxels for which the traverse is equal to one to have the mass found in the pixel for that ray. These voxels may be eliminated from the volume of interest and the cumulative masses associated with the area-image sensors are corrected accordingly in step 56. This process is monitored by unit 57 and the whole process is then repeated, as required, until no further eliminations are effected, whereupon the algorithm proceeds to step 58, wherein the RATIOS of mass/volume are calculated for each pixel (or ray) in all of the images. This calculation is performed also in respect of the unit-length pixels since their associated voxels were also within the volume of interest prior to being eliminated.

In step 59, the RATIOS are compared with each other so as to determine the maximum ratio, corresponding to the maximum lower-bound density within the test volume. As each ray has at least two voxels along it, the density cannot be assigned to any given voxel, it merely being known that the density applies only to voxels along that ray and not to remaining voxels within the volume of interest. In step 60, the maximum ratio is compared with a LIMIT corresponding to the density threshold of a nitrogenous explosive material. If the maximum ratio exceeds the LIMIT, the algorithm exits at [4], whereupon an alarm is sounded, and the suitcase may then be examined manually.

If the maximum ratio does not exceed the LIMIT, the algorithm proceeds to step 61, which checks whether there is more than one body in the test volume. If not, the algorithm exists at [12], whereupon the process is complete and the suitcase is identified as not representing a security risk.

If, in step 61, it is determined that there exists more than one body, then the algorithm proceeds to step 62 which finds a maximal ratio for each body and identifies a body B having the lowest maximal ratio R. The body B corresponds to the body least likely to have an actual density above the limit density and is thus eliminated in step 63.

Step 63 eliminates the body B which has contributed to the images separately on at least one of the area-image sensors 30, 31 and 32 whilst overlapping other bodies on the other area-image sensors. The body B cannot simply be ignored and in step 63 the whole body B is filled with the density equal to the calculated lowest maximal ratio R. This, of course, is an approximation but the errors have only a small effect on the denser bodies remaining.

Step 64 now corrects the images by subtracting the contribution of the body B which has now been eliminated. This subtraction may cause several pixels to have new cumulative masses below the threshold $T_1$ which previously exceeded the threshold. The boundary 19 has therefore to be corrected and new cones defined. The corrected images and boundaries are now fed to step 50 as input.

The procedure continues until a body is found whose maximal ratio exceeds the LIMIT, or until the last (i.e. densest) body is found to have a maximal ratio not exceeding the LIMIT.

It will be clear from what has been described above that there are only two exits in the algorithm, namely [4] and [12]. The algorithm exits at [4] as soon as a body is encountered whose lower-bound density exceeds the LIMIT. This condition represents a security risk wherein the identified body is assumed to contain a nitrogenous explosive and therefore no further processing is required. On the other hand, when the algorithm exits at [12], this is not an absolute indication that the test volume does not contain a nitrogenous explosive but, rather, merely indicates that it does not contain a nitrogenous explosive large and dense enough to be detected. This avoids raising an alarm in the event that a suitcase is examined which may possibly contain an explosive but not in a sufficient quantity to cause significant damage.

It will be apparent to those skilled in the art that the algorithm described with reference to FIGS. 6a, 6b, 7 and 8 of the drawings is merely representative of a generalized approach to the determination of the maximum lower-bound density within a volume of interest. Thus, for example, during the "elimination" process wherein voxels are successively eliminated from the test volume and the cumulative masses associated with these voxels corrected accordingly, the order of correction and elimination is arbitrary. Thus, if desired, the voxels may, in a first stage, merely be identified as being associated with a unit traverse and the whole process of correcting the image data may then be affirmed after all such voxels have been so identified.

In the embodiment described above with relation to FIGS. 6a, 6b and 6c, 7 and 8 of the drawings, it has been assumed that the LIMIT is invariant. In practice, if the signal noise is large, the LIMIT may be adjusted so as to increase with the variance of the data and decrease with the amount of radiation reaching the area-image sensor and with the traverse length. This reduces the number of false detections based on data noise instead of real data.

Figure 9:
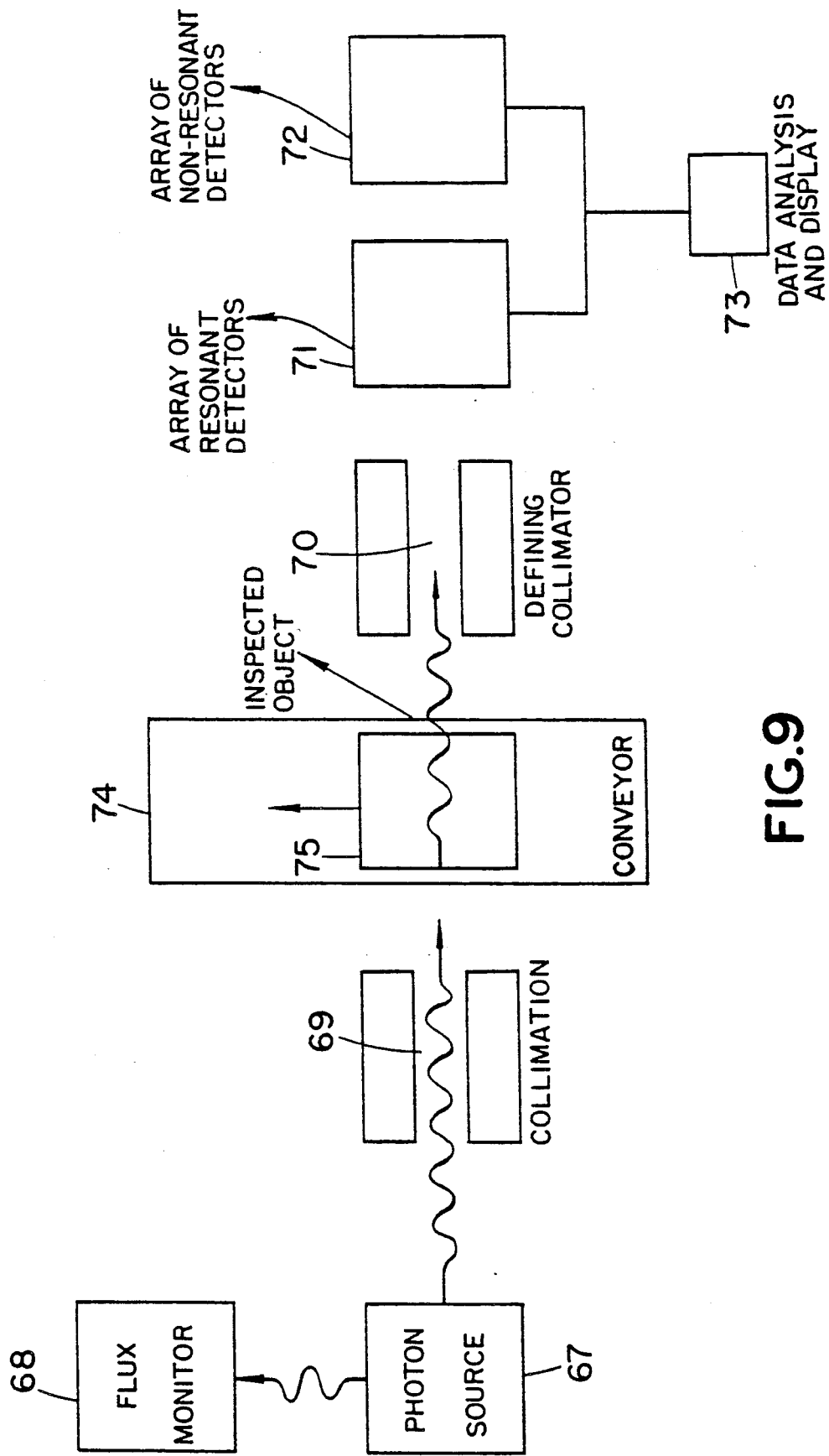
FIG. 9 shows a system for detecting a nitrogenous explosive material using the method shown in the flow diagram of FIGS. 6a, 6b, 7 and 8.

Referring now to FIG. 9 of the drawings there will be described a system for detecting a nitrogenous explosive employing the algorithm according to the invention.

FIG. 9 shows a block diagram of an installation according to the invention with resonant and non-resonant detectors. As shown, the system comprises a $\gamma$-ray emitter 67 serving as a 9.17 MeV photon source and linked to a flux monitor 68. There are further provided collimator blocks 69 and 70 for the collimation of the $\gamma$-radiation emitted from the photon source 67 in front of and behind the inspected object. The system further comprises an array 71 of resonant detectors and an array 72 of non-resonant detectors, both linked to a data analysis and display device 73 which is also coupled to the flux monitor 68 in a manner not shown.

The system is associated with a conveyer 74 adapted to move successively a plurality of objects such as an object 75 across the beam emitted by the photon source 67. After its encounter with the object 75 the passing radiation is once more collimated by a collimator lens 70 and is thereupon analysed by the arrays of resonant detectors 71, non-resonant detectors 72 and the data analysis device 73.

As we explained in the opening section of this specification, the resonant attenuations of the incident photon flux are detected on an array of detectors having a nitrogen rich detecting medium. These detectors are constituted by the array 71 of resonant detectors. Since, however, in addition to the resonant attenuation there also occurs a conventional non-resonant attenuation, the array 72 of non-resonant detectors is also provided in order to factor-out this component in the spectrum which is then used for normalization purposes. Instead of non-resonant detectors, it is also possible to make use of Compton electrons produced in the resonant detector by photons of all energies for factoring out the non-resonant attenuation component.

The array of resonant detectors 71, comprises an area image sensor having a plurality of pixels thereon for indicating the cumulative mass along the line of sight of each ray striking a pixel. Thus, each pixel indicates the cumulative mass associated with a respective incident ray. However, it also possible to employ other types of sensor, such as suitable crystals, bubble chambers and so on, and to provide separate means for determining the line of sight of each incident ray striking the sensor.

The system shown in FIG. 7 operates as follows. The photon source 67 produces a plurality of rays of penetrating radiation each of which penetrates the object 75 so as to generate output data proportional to the cumulative mass of nitrogen encountered along the path of the respective ray. The flux monitor 68 operates in conjunction with the photon source 67 in order to ensure that the photon source 67 generates $\gamma$-rays having an energy of 9.17 MeV, corresponding to the energy level of $^{14}N$ susceptible to resonant attenuation.

In such an arrangement, the data analysis device 73 includes a computer programmed according to the algorithm described above with reference to FIGS. 2 to 6 of the drawings for determining the maximum lower-bound density of nitrogen ($^{14}N$) in the scanned object 75. The calculated value is compared with a predetermined first threshold corresponding to the maximum safe (i.e. non-explosive) nitrogen density and a warning is generated if the calculated maximum lower-bound density exceeds the first threshold.

In an airport security system it is important not to raise such an alarm unless the calculated maximum lower-bound nitrogen density is commensurate with an explosive of sufficient mass to constitute a security risk. The data analysis and display device 73 is therefore programmed to ignore a body within the scanned object 75 whose mass is less than a predetermined second threshold.

Whilst the invention has been described with particular regard to an airport security system for identifying suitcases containing explosives, it will be clear that the algorithm has much more general use for discriminating between different bodies according to their density.

It will also be appreciated that whilst the invention has been described with particular reference to the determination of mass-density, the algorithm may be used for the determination of properties other than mass and mass-density; it being only required that the cumulative amount of the required property is given in several directions and that it is required only to determine the body with the highest property-density, a lower-bound on that property-density being sufficient.

Finally, whilst the system according to the invention has been described with regard to a suitably programmed computer, it will readily be understood that this is not a requirement and that discrete processing means can be provided for carrying out the method according to the invention.

We claim:

1. A method of determining a lower-bound mass-density of a substance within a volume of interest of a body, the method comprising the steps of:

scanning a volume of interest of said body with radiation from at least one source of radiation in a predetermined number of directions so as to derive for each direction an area having a plurality of projections thereon each representing a cumulative value of a mass of said substance within the volume of interest along a respective one of the projections wherein said areas bound volume elements contained in said body, determining an estimated volume of the body as an intersection of all volume elements bounded by said areas, comparing for each area the sum of all the projections and applying correction as required so as to remove any disparity between said sums and produce a uniform sum in each one of said directions, and determining the lower-bound mass-density of the substance of the body as the quotient of the uniform sum divided by the estimated volume.

2. The method according to claim 1, wherein each area is subdivided into a plurality of elemental areas (pixels) each corresponding to one of the projections and the volume of interest is subdivided into a plurality of elemental volumes (voxels) each bounded by respective ones of said elemental areas, the estimated volume being determined by the sum of elemental volumes for which the projection therethrough is greater than zero in all of the elemental areas bounding said elemental volume.

3. The method according to claim 2, wherein the volume of interest is scanned by passing therethrough a plurality of rays of penetrating radiation so as to derive respective image data of said body relating to said cumulative value of said mass along the respective projections.

4. The method according to claim 3, wherein the image data of the body is derived on a plurality of area-image sensors, each corresponding to a respective one of said areas and having a plurality of pixels thereon, each pixel being energized by a respective one of said rays striking the pixel after passing through the body as a function of the cumulative value of said mass along the respective projections.

5. The method according to claim 4, wherein the penetrating radiation is sensitive to density of nitrogen and each pixel is energized as a function of a cumulative nitrogen mass within the volume of interest along the respective projections.

6. The method according to claim 5, wherein the rays are derived from a fan beam of radiation and there is provided the further step of correcting the image data so as to compensate for magnification thereof produced by the beam.

7. The method according to claim 3, wherein each area is subdivided into a plurality of elemental areas each corresponding to one of the projections and the volume is subdivided into a plurality of elemental volumes (voxels) each bounded by respective ones of said elemental areas, and further comprising the steps of:

(a) determining for each ray passing through the body its traverse given by the number of voxels intersected by the body in the path of the ray, (b) identifying all those rays whose traverse equals one, (c) associating with each one of the voxels intersected by the rays identified in (b) the cumulative value of said mass along the respective projection, (d) determining for each of the voxels identified in (c) the mass-density given by the mass value associated therewith in (c) divided by its volume, (e) recording the voxel mass-density derived in (d), (f) for each voxel identified in (c), subtracting the mass value associated therewith from the cumulative mass values associated with all rays passing therethrough, (g) for all rays having mass associated therewith, repeating steps (a) to (f) until no rays remain having a traverse equal to one, (h) if all voxels have been eliminated, determining the maximum lower-bound mass-density as the maximum voxel mass-density recorded in (e), (i) if there are remaining voxels, determining for each ray the ratio of the cumulative mass value associated therewith to the number of voxels intersected thereby, (j) recording the ratios derived in (i), (k) determining the highest ratio recorded in (j) as the highest lower-bound mass-density value within the volume of interest, (l) dividing the voxels identified in (c) into discrete contiguous elements, (m) determining for each one of the discrete elements identified in (l) the highest ratio recorded in (j) so as to derive a plurality of highest ratios each relating to a respective one of said elements, (n) recording the highest ratios determined in (m), (o) determining a pixel having the lowest ratio recorded in (n), (p) determining the discrete element relating to the pixel determined in (o), (q) determining all voxels associated with the discrete elements determined in (p), (r) substituting for all the voxels determined in (q) the lowest ratio recorded in (n), (s) eliminating from the volume of interest the element determined in (p) and subtracting from all the pixels associated therewith the respective mass values contributed by said element as corrected in step (r), (t) repeating steps (i) to (s) until only one element remains, (u) determining for each ray intersecting the last element the ratio of the cumulative mass value associated therewith to the number of voxels intersected thereby, and (v) recording the ratios derived in (u).

8. The method according to claim 7, for determining whether an element in the volume of interest has a mass-density exceeding a predetermined first threshold, wherein the mass-densities derived in (d) and the ratios derived in (i) are compared with said first threshold and processing terminates in the event that one of said mass-densities or one of said ratios exceeds the first threshold.

9. The method according to claim 7, for determining whether an element in the volume of interest has a mass-density exceeding a predetermined first threshold, wherein the mass-densities derived in (d) and the ratios derived in (u) are compared with said first threshold and processing terminates in the event that one of said mass-densities or one of said ratios exceeds the first threshold.

10. The method according to claim 8, for determining whether the lower-bound mass-density exceeds said predetermined first threshold and a total mass of said substance within the volume of interest exceeds a predetermined second threshold, wherein respective regions of interest are determined on each of the area-image sensors for which respective ones of said pixels have a total energy content corresponding to the cumulative value of said mass exceeding said second threshold and said volume of interest is determined by respective cones emanating from respective sources of said radiation and bounded by corresponding ones of said regions of interest.

11. The method according to claim 7, wherein the image data for each area is processed successively, the value of mass associated with each voxel identified in step (c) being subtracted from the respective cumulative mass values after each area has been completely processed.

12. The method according to claim 7, further comprising the steps of:

(w) pre-processing the image data associated with each area so as to derive therefor at least one discrete region associated with a respective element whose lower-bound mass-density is required to be determined, (y) determining all voxels in the volume of interest for which at least one ray passing therethrough strikes a corresponding image sensor outside at least one respective region, and (z) employing the steps (a) to (v) on all voxels in the volume of interest which have not been determined in step (y).

13. The method according to claim 8, for warning whether the lower-bound mass-density value of a body within the volume of interest containing at least one element exceeds said predetermined first threshold, comprising:

(a) successively determining the lower-bound mass-density of all elements within the volume of interest, (b) comparing each successive value derived in step (a) with said first threshold, (c) generating a warning signal if the value derived in step (a) exceeds said first threshold, and (d) repeating steps (a) to (c) as required.

14. The method according to claim 8, wherein the densities derived in (d) and the ratios derived in (i) are compared with a third threshold being a function of the first threshold, a data noise level, the traverse for the respective ray and a respective pixel energization.

15. The method according to claim 9, wherein the densities derived in (d) and the ratios derived in (u) are compared with a third threshold being a function of the first threshold, a data noise level, the traverse for the respective ray and a respective pixel energization.

16. A system for determining a lower-bound mass-density of a substance in a body, the system comprising:

scanning means including at least one radiation source, for scanning a volume of interest of said body in a predetermined number of directions so as to derive for each direction an area having a plurality of projections thereon each representing a cumulative value of a mass within the volume of interest along a respective one of the projections, wherein said areas bound volume elements contained in said body, a plurality of sensors responsive to the scanning means and each disposed in relation thereto for detecting the projections in a respective one of said directions, volume determination means coupled to the sensors for determining an estimated volume of the body as an intersection of all volume elements bounded by said areas, comparator means coupled to the sensors for comparing for each area the sum of all the projections and applying correction as required so as to remove any disparity between said sums and produce a uniform sum in each one of said directions, and computing means coupled to the sensors, the volume determination means and the comparator means for determining the lower-bound mass-density of the substance as the quotient of the uniform sum divided by the estimated volume.

17. The system according to claim 16, wherein the radiation source is adapted to generate a plurality of rays of penetrating radiation so as to derive respective image data relating to the cumulative value of said mass along the respective projections.

18. The system according to claim 17, wherein the sensors are area-image sensors, each corresponding to a respective one of said areas and having a plurality of pixels thereon, each pixel being energized by a respective one of said rays striking the pixel after passing through the body as a function of the cumulative value of said mass along the respective projections.

19. The system according to claim 18, wherein the penetrating radiation is sensitive to a mass density of nitrogen and each pixel is energized as a function of the cumulative nitrogen mass within the volume of interest along the respective projections.

20. The system according to claim 17, wherein the rays are derived from a fan beam of radiation and there are further provided means for correcting the image data so as to compensate for magnification thereof produced by the beam.

21. The system according to claim 17, wherein:

each area is subdivided into a plurality of elemental areas each corresponding to one of the projections and the volume is subdivided into a plurality of elemental volumes each bounded by respective ones of said elemental areas, and the volume determination means, the comparator means and the computing means are constituted by a computer including:
(a) means for determining for each ray passing through the body its traverse given by the number of voxels intersected by the body in the path of the ray,
(b) means for identifying all those rays whose traverse equals one,
(c) means for associating with each one of the voxels intersected by the rays identified in (b) the cumulative value of said mass along the respective projection,
(d) means for determining for each of the voxels identified in (c) the mass-density given by the mass value associated therewith in (c) divided by its volume,
(e) recording means for recording the voxel mass-density derived in (d),
(f) subtracting means for subtracting for each voxel identified in (c), the value associated therewith from the cumulative mass values associated with all rays passing therethrough,
(g) means for determining the maximum lower-bound mass-density as the maximum voxel mass-density recorded in (e),
(h) means for determining for each ray the ratio of the cumulative mass value associated therewith to the number of voxels intersected thereby,
(i) recording means for recording the ratios derived in (h),
(j) means for determining the highest ratio recorded in (i) as the highest lower-bound mass-density value within the volume of interrst,
(k) means for dividing the voxels identified in (c) into discrete contiguous elements,
(l) means for determining for each one of the discrete elements identified in (k) the highest ratio recorded in (i) so as to derive a plurality of highest ratios each relating to a respective one of said elements,
(m) recording means for recording the highest ratios determined in (l),
(n) means for determining a pixel having the lowest ratio recorded in (m),
(o) means for determining the discrete element relating to the pixel determined in (n),
(p) means for determining all voxels associated with the discrete elements determined in (o),
(q) means for substituting for all the voxels determined in (p) the lowest ratio recorded in (m), and
(r) means for eliminating from the volume of interest the element determined in (o) and subtracting from all the pixels associated therewith the respective values contributed by said element as corrected in step (q).

22. The system according to claim 21, for determining whether an element within the volume of interest has a mass-density value exceeding a predetermined first threshold, including means for comparing the mass-densities derived in (d) and the ratios derived in (h) with said first threshold and for generating a signal in the event that one of said mass-densities or one of said ratios exceeds the first threshold.

23. The system according to claim 21, further comprising:
(a) means for processing the image data associated with each area so as to derive therefor at least one discrete region associated with a respective body whose lower-bound mass density is required to be determined, and
(b) means for determining all voxels in the volume of interest for which at least one ray passing therethrough strikes the corresponding image sensor outside the respective region.

24. The system according to claim 22, for warning whether the lower-bound mass-density value of a body within the volume of interst containing at least one element exceeds said predetermined first threshold, the system further comprising:
(a) means for successively determining the lower-bound mass-density of all elements within the volume of interst,
(b) means for comparing each successive value derived in step (a) with said first threshold,
(c) means for generating a warning signal if the value derived in step (a) exceeds said first threshold.

25. The system according claim 21, wherein there are further provided means for adjusting the first threshold as a function of a data noise level, a traverse for the respective ray and a respective pixel energization.

26. A method of determining a lower-bound value of a physical property per unit volume of a body, the method comprising the steps of:

scanning a volume of interest of said body with radiation from at least one source of radiation in a predetermined number of directions so as to derive for each direction an area having a plurality of projections thereon each representing a cumulative value of said property within the volume of interest along a respective one of the projections, wherein said areas bound volume elements contained in said body, determining an estimated volume of the body as an intersection of all volume elements bounded by said areas, comparing for each area the sum of all the projections and applying correction as required so as to remove any disparity between said sums and produce a uniform sum in each one of said directions, and determining the lower-bound value of said property of the body per unit volume as the quotient of the uniform sum divided by the estimated volume.

27. The method according to claim 26, wherein each area is subdivided into a plurality of elemental areas (pixels) each corresponding to one of the projections and the volume of interest is subdivided into a plurality of elemental volumes (voxels) each bounded by respective ones of said elemental areas, the estimated volume being determined by the sum of elemental volumes for which the projection therethrough is greater than zero in all of the elemental areas bounding said elemental volume.

28. A system for determining a lower-bound value of a physical property per unit volume of a body, the system comprising:

scanning means including a radiation surce for scanning a volume of interest of said body in a predetermined number of directions so as to derive for each direction an area having a plurality of projections thereon each representing a cumulative value of said property within the volume of interest along a respective one of the projections, wherein said areas bound volume elements contained in said body, a plurality of sensors responsive to the scanning means and each disposed in relation thereto for detecting the projections in a respective one of said directions, volume determination means coupled to the sensors for determining an estimated volume of the body as an intersection of all volume elements bounded by said areas, comparator means coupled to the sensors for comparing for each area the sum of all the projections and applying correction as required so as to remove any disparity between said sums and produce a uniform sum in each one of said directions, and computing means coupled to the sensors, the volume determination means and the comparator means for determining the lower-bound value of said property per unit volume of the body as the quotient of the uniform sum divided by the estimated volume.

29. The system according to claim 28, wherein the radiation source is adapted to generate a plurality of rays of penetrating radiation so as to derive respective image data relating to the cumulative value of said physical property along the respective projections.

30. The method according to claim 9, for determining whether the lower-bound mass-density exceeds said predetermined first threshold and a total mass of said substance within the volume of interest exceeds a predetermined second threshold, wherein respective regions of interest are determined on each of the area-image sensors for which respective ones of said pixels have a total energy content corresponding to the cumulative value of said mass exceeding said second threshold and said volume of interest is determined by respective cones emanating from respective sources of said radiation and bounded by corresponding ones of said regions of interest.

* * * * *